United States Patent
Crawford

(10) Patent No.: US 12,064,189 B2
(45) Date of Patent: Aug. 20, 2024

(54) NAVIGATED INSTRUMENT FOR USE IN ROBOTIC GUIDED SURGERY

(71) Applicant: GLOBUS MEDICAL, INC., Audubon, PA (US)

(72) Inventor: Neil Crawford, Chandler, AZ (US)

(73) Assignee: Globus Medical, Inc., Audubon, PA (US)

( * ) Notice: Subject to any disclaimer, the term of this patent is extended or adjusted under 35 U.S.C. 154(b) by 590 days.

(21) Appl. No.: 17/120,879

(22) Filed: Dec. 14, 2020

(65) Prior Publication Data

US 2021/0177525 A1 Jun. 17, 2021

Related U.S. Application Data

(60) Provisional application No. 62/947,688, filed on Dec. 13, 2019.

(51) Int. Cl.
*A61B 34/20* (2016.01)
*A61B 34/30* (2016.01)
*A61B 90/00* (2016.01)

(52) U.S. Cl.
CPC .............. *A61B 34/20* (2016.02); *A61B 34/30* (2016.02); *A61B 90/39* (2016.02); *A61B 2034/2055* (2016.02)

(58) Field of Classification Search
CPC ......... A61B 34/20; A61B 34/30; A61B 90/39; A61B 2034/2055; A61B 2090/3983
See application file for complete search history.

(56) References Cited

U.S. PATENT DOCUMENTS

| | | |
|---|---|---|
| 1,068,626 A | 7/1913 | Buck |
| 4,150,293 A | 4/1979 | Franke |
| 4,737,038 A | 4/1988 | Dostoomian |
| 4,757,710 A | 7/1988 | Haynes |
| 5,246,010 A | 9/1993 | Gazzara et al. |
| 5,354,314 A | 10/1994 | Hardy et al. |
| 5,397,323 A | 3/1995 | Taylor et al. |
| 5,598,453 A | 1/1997 | Baba et al. |
| 5,772,594 A | 6/1998 | Barrick |
| 5,791,908 A | 8/1998 | Gillio |
| 5,820,559 A | 10/1998 | Ng et al. |
| 5,825,982 A | 10/1998 | Wright et al. |
| 5,887,121 A | 3/1999 | Funda et al. |
| 5,911,449 A | 6/1999 | Daniele et al. |
| 5,951,475 A | 9/1999 | Gueziec et al. |
| 5,987,960 A | 11/1999 | Messner et al. |
| 6,012,216 A | 1/2000 | Esteves et al. |
| 6,031,888 A | 2/2000 | Ivan et al. |

(Continued)

OTHER PUBLICATIONS

US 8,231,638 B2, 07/2012, Swarup et al. (withdrawn)

*Primary Examiner* — Baisakhi Roy
*Assistant Examiner* — Kaitlyn E Sebastian

(57) ABSTRACT

An instrument for use in a navigated surgical procedure, the instrument includes a proximal portion, a distal portion and a shaft extending therebetween. An angled instrument tip is positioned at an end of the distal portion of the instrument. A first tracking array is coupled to the proximal portion of the instrument and a surveillance array is coupled to the proximal portion of the instrument. The tracking array includes a plurality of tracking markers, and is configured to rotate with respect to a central axis of the instrument.

17 Claims, 9 Drawing Sheets

(56) References Cited

U.S. PATENT DOCUMENTS

| | | |
|---|---|---|
| 6,033,415 A | 3/2000 | Mittelstadt et al. |
| 6,080,181 A | 6/2000 | Jensen et al. |
| 6,106,511 A | 8/2000 | Jensen |
| 6,122,541 A | 9/2000 | Cosman et al. |
| 6,144,875 A | 11/2000 | Schweikard et al. |
| 6,157,853 A | 12/2000 | Blume et al. |
| 6,167,145 A | 12/2000 | Foley et al. |
| 6,167,292 A | 12/2000 | Badano et al. |
| 6,201,984 B1 | 3/2001 | Funda et al. |
| 6,203,196 B1 | 3/2001 | Meyer et al. |
| 6,205,411 B1 | 3/2001 | DiGioia, III et al. |
| 6,212,419 B1 | 4/2001 | Blume et al. |
| 6,231,565 B1 | 5/2001 | Tovey et al. |
| 6,236,875 B1 | 5/2001 | Bucholz et al. |
| 6,246,900 B1 | 6/2001 | Cosman et al. |
| 6,301,495 B1 | 10/2001 | Gueziec et al. |
| 6,306,126 B1 | 10/2001 | Montezuma |
| 6,312,435 B1 | 11/2001 | Wallace et al. |
| 6,314,311 B1 | 11/2001 | Williams et al. |
| 6,320,929 B1 | 11/2001 | Von Der Haar |
| 6,322,567 B1 | 11/2001 | Mittelstadt et al. |
| 6,325,808 B1 | 12/2001 | Bernard et al. |
| 6,340,363 B1 | 1/2002 | Bolger et al. |
| 6,377,011 B1 | 4/2002 | Ben-Ur |
| 6,379,302 B1 | 4/2002 | Kessman et al. |
| 6,402,762 B2 | 6/2002 | Hunter et al. |
| 6,424,885 B1 | 7/2002 | Niemeyer et al. |
| 6,447,503 B1 | 9/2002 | Wynne et al. |
| 6,451,027 B1 | 9/2002 | Cooper et al. |
| 6,477,400 B1 | 11/2002 | Barrick |
| 6,484,049 B1 | 11/2002 | Seeley et al. |
| 6,487,267 B1 | 11/2002 | Wolter |
| 6,490,467 B1 | 12/2002 | Bucholz et al. |
| 6,490,475 B1 | 12/2002 | Seeley et al. |
| 6,499,488 B1 | 12/2002 | Hunter et al. |
| 6,501,981 B1 | 12/2002 | Schweikard et al. |
| 6,507,751 B2 | 1/2003 | Blume et al. |
| 6,535,756 B1 | 3/2003 | Simon et al. |
| 6,560,354 B1 | 5/2003 | Maurer, Jr. et al. |
| 6,565,554 B1 | 5/2003 | Niemeyer |
| 6,587,750 B2 | 7/2003 | Gerbi et al. |
| 6,614,453 B1 | 9/2003 | Suri et al. |
| 6,614,871 B1 | 9/2003 | Kobiki et al. |
| 6,619,840 B2 | 9/2003 | Rasche et al. |
| 6,636,757 B1 | 10/2003 | Jascob et al. |
| 6,645,196 B1 | 11/2003 | Nixon et al. |
| 6,666,579 B2 | 12/2003 | Jensen |
| 6,669,635 B2 | 12/2003 | Kessman et al. |
| 6,701,173 B2 | 3/2004 | Nowinski et al. |
| 6,757,068 B2 | 6/2004 | Foxlin |
| 6,782,287 B2 | 8/2004 | Grzeszczuk et al. |
| 6,783,524 B2 | 8/2004 | Anderson et al. |
| 6,786,896 B1 | 9/2004 | Madhani et al. |
| 6,788,018 B1 | 9/2004 | Blumenkranz |
| 6,804,581 B2 | 10/2004 | Wang et al. |
| 6,823,207 B1 | 11/2004 | Jensen et al. |
| 6,827,351 B2 | 12/2004 | Graziani et al. |
| 6,837,892 B2 | 1/2005 | Shoham |
| 6,839,612 B2 | 1/2005 | Sanchez et al. |
| 6,856,826 B2 | 2/2005 | Seeley et al. |
| 6,856,827 B2 | 2/2005 | Seeley et al. |
| 6,879,880 B2 | 4/2005 | Nowlin et al. |
| 6,892,090 B2 | 5/2005 | Verard et al. |
| 6,920,347 B2 | 7/2005 | Simon et al. |
| 6,922,632 B2 | 7/2005 | Foxlin |
| 6,968,224 B2 | 11/2005 | Kessman et al. |
| 6,978,166 B2 | 12/2005 | Foley et al. |
| 6,988,009 B2 | 1/2006 | Grimm et al. |
| 6,991,627 B2 | 1/2006 | Madhani et al. |
| 6,996,487 B2 | 2/2006 | Jutras et al. |
| 6,999,852 B2 | 2/2006 | Green |
| 7,007,699 B2 | 3/2006 | Martinelli et al. |
| 7,016,457 B1 | 3/2006 | Senzig et al. |
| 7,043,961 B2 | 5/2006 | Pandey et al. |
| 7,062,006 B1 | 6/2006 | Pelc et al. |
| 7,063,705 B2 | 6/2006 | Young et al. |
| 7,072,707 B2 | 7/2006 | Galloway, Jr. et al. |
| 7,083,615 B2 | 8/2006 | Peterson et al. |
| 7,097,640 B2 | 8/2006 | Wang et al. |
| 7,099,428 B2 | 8/2006 | Clinthorne et al. |
| 7,108,421 B2 | 9/2006 | Gregerson et al. |
| 7,130,676 B2 | 10/2006 | Barrick |
| 7,139,418 B2 | 11/2006 | Abovitz et al. |
| 7,139,601 B2 | 11/2006 | Bucholz et al. |
| 7,155,316 B2 | 12/2006 | Sutherland et al. |
| 7,164,968 B2 | 1/2007 | Treat et al. |
| 7,167,738 B2 | 1/2007 | Schweikard et al. |
| 7,169,141 B2 | 1/2007 | Brock et al. |
| 7,172,627 B2 | 2/2007 | Fiere et al. |
| 7,194,120 B2 | 3/2007 | Wicker et al. |
| 7,197,107 B2 | 3/2007 | Arai et al. |
| 7,231,014 B2 | 6/2007 | Levy |
| 7,231,063 B2 | 6/2007 | Naimark et al. |
| 7,239,940 B2 | 7/2007 | Wang et al. |
| 7,248,914 B2 | 7/2007 | Hastings et al. |
| 7,301,648 B2 | 11/2007 | Foxlin |
| 7,302,288 B1 | 11/2007 | Schellenberg |
| 7,313,430 B2 | 12/2007 | Urquhart et al. |
| 7,318,805 B2 | 1/2008 | Schweikard et al. |
| 7,318,827 B2 | 1/2008 | Leitner et al. |
| 7,319,897 B2 | 1/2008 | Leitner et al. |
| 7,324,623 B2 | 1/2008 | Heuscher et al. |
| 7,327,865 B2 | 2/2008 | Fu et al. |
| 7,331,967 B2 | 2/2008 | Lee et al. |
| 7,333,642 B2 | 2/2008 | Green |
| 7,339,341 B2 | 3/2008 | Oleynikov et al. |
| 7,366,562 B2 | 4/2008 | Dukesherer et al. |
| 7,379,790 B2 | 5/2008 | Toth et al. |
| 7,386,365 B2 | 6/2008 | Nixon |
| 7,422,592 B2 | 9/2008 | Morley et al. |
| 7,435,216 B2 | 10/2008 | Kwon et al. |
| 7,440,793 B2 | 10/2008 | Chauhan et al. |
| 7,460,637 B2 | 12/2008 | Clinthorne et al. |
| 7,466,303 B2 | 12/2008 | Yi et al. |
| 7,493,153 B2 | 2/2009 | Ahmed et al. |
| 7,505,617 B2 | 3/2009 | Fu et al. |
| 7,533,892 B2 | 5/2009 | Schena et al. |
| 7,542,791 B2 | 6/2009 | Mire et al. |
| 7,555,331 B2 | 6/2009 | Viswanathan |
| 7,567,834 B2 | 7/2009 | Clayton et al. |
| 7,594,912 B2 | 9/2009 | Cooper et al. |
| 7,606,613 B2 | 10/2009 | Simon et al. |
| 7,607,440 B2 | 10/2009 | Coste-Maniere et al. |
| 7,623,902 B2 | 11/2009 | Pacheco |
| 7,630,752 B2 | 12/2009 | Viswanathan |
| 7,630,753 B2 | 12/2009 | Simon et al. |
| 7,643,862 B2 | 1/2010 | Schoenefeld |
| 7,660,623 B2 | 2/2010 | Hunter et al. |
| 7,661,881 B2 | 2/2010 | Gregerson et al. |
| 7,683,331 B2 | 3/2010 | Chang |
| 7,683,332 B2 | 3/2010 | Chang |
| 7,689,320 B2 | 3/2010 | Prisco et al. |
| 7,691,098 B2 | 4/2010 | Wallace et al. |
| 7,702,379 B2 | 4/2010 | Avinash et al. |
| 7,702,477 B2 | 4/2010 | Tuemmler et al. |
| 7,711,083 B2 | 5/2010 | Heigl et al. |
| 7,711,406 B2 | 5/2010 | Kuhn et al. |
| 7,720,523 B2 | 5/2010 | Omernick et al. |
| 7,725,253 B2 | 5/2010 | Foxlin |
| 7,726,171 B2 | 6/2010 | Langlotz et al. |
| 7,742,801 B2 | 6/2010 | Neubauer et al. |
| 7,751,865 B2 | 7/2010 | Jascob et al. |
| 7,760,849 B2 | 7/2010 | Zhang |
| 7,762,825 B2 | 7/2010 | Burbank et al. |
| 7,763,015 B2 | 7/2010 | Cooper et al. |
| 7,787,699 B2 | 8/2010 | Mahesh et al. |
| 7,796,728 B2 | 9/2010 | Bergfjord |
| 7,813,838 B2 | 10/2010 | Sommer |
| 7,818,044 B2 | 10/2010 | Dukesherer et al. |
| 7,819,859 B2 | 10/2010 | Prisco et al. |
| 7,824,401 B2 | 11/2010 | Manzo et al. |
| 7,831,294 B2 | 11/2010 | Viswanathan |
| 7,834,484 B2 | 11/2010 | Sartor |
| 7,835,557 B2 | 11/2010 | Kendrick et al. |

(56) References Cited

U.S. PATENT DOCUMENTS

| | | |
|---|---|---|
| 7,835,778 B2 | 11/2010 | Foley et al. |
| 7,835,784 B2 | 11/2010 | Mire et al. |
| 7,840,253 B2 | 11/2010 | Tremblay et al. |
| 7,840,256 B2 | 11/2010 | Akin et al. |
| 7,843,158 B2 | 11/2010 | Prisco |
| 7,844,320 B2 | 11/2010 | Shahidi |
| 7,853,305 B2 | 12/2010 | Simon et al. |
| 7,853,313 B2 | 12/2010 | Thompson |
| 7,865,269 B2 | 1/2011 | Prisco et al. |
| D631,966 S | 2/2011 | Perloff et al. |
| 7,879,045 B2 | 2/2011 | Gielen et al. |
| 7,881,767 B2 | 2/2011 | Strommer et al. |
| 7,881,770 B2 | 2/2011 | Melkent et al. |
| 7,886,743 B2 | 2/2011 | Cooper et al. |
| RE42,194 E | 3/2011 | Foley et al. |
| RE42,226 E | 3/2011 | Foley et al. |
| 7,900,524 B2 | 3/2011 | Calloway et al. |
| 7,907,166 B2 | 3/2011 | Lamprecht et al. |
| 7,909,122 B2 | 3/2011 | Schena et al. |
| 7,925,653 B2 | 4/2011 | Saptharishi |
| 7,930,065 B2 | 4/2011 | Arkin et al. |
| 7,935,130 B2 | 5/2011 | Williams |
| 7,940,999 B2 | 5/2011 | Liao et al. |
| 7,945,012 B2 | 5/2011 | Ye et al. |
| 7,945,021 B2 | 5/2011 | Shapiro et al. |
| 7,953,470 B2 | 5/2011 | Vetter et al. |
| 7,954,397 B2 | 6/2011 | Choi et al. |
| 7,971,341 B2 | 7/2011 | Dukesherer et al. |
| 7,974,674 B2 | 7/2011 | Hauck et al. |
| 7,974,677 B2 | 7/2011 | Mire et al. |
| 7,974,681 B2 | 7/2011 | Wallace et al. |
| 7,979,157 B2 | 7/2011 | Anvari |
| 7,983,733 B2 | 7/2011 | Viswanathan |
| 7,988,215 B2 | 8/2011 | Seibold |
| 7,996,110 B2 | 8/2011 | Lipow et al. |
| 8,004,121 B2 | 8/2011 | Sartor |
| 8,004,229 B2 | 8/2011 | Nowlin et al. |
| 8,010,177 B2 | 8/2011 | Csavoy et al. |
| 8,019,045 B2 | 9/2011 | Kato |
| 8,021,310 B2 | 9/2011 | Sanborn et al. |
| 8,035,685 B2 | 10/2011 | Jensen |
| 8,046,054 B2 | 10/2011 | Kim et al. |
| 8,046,057 B2 | 10/2011 | Clarke |
| 8,052,688 B2 | 11/2011 | Wolf, II |
| 8,054,184 B2 | 11/2011 | Cline et al. |
| 8,054,752 B2 | 11/2011 | Druke et al. |
| 8,057,397 B2 | 11/2011 | Li et al. |
| 8,057,407 B2 | 11/2011 | Martinelli et al. |
| 8,062,288 B2 | 11/2011 | Cooper et al. |
| 8,062,375 B2 | 11/2011 | Glerum et al. |
| 8,066,524 B2 | 11/2011 | Burbank et al. |
| 8,073,335 B2 | 12/2011 | Labonville et al. |
| 8,079,950 B2 | 12/2011 | Stern et al. |
| 8,086,299 B2 | 12/2011 | Adler et al. |
| 8,092,370 B2 | 1/2012 | Roberts et al. |
| 8,098,914 B2 | 1/2012 | Liao et al. |
| 8,100,950 B2 | 1/2012 | St. Clair et al. |
| 8,105,320 B2 | 1/2012 | Manzo |
| 8,108,025 B2 | 1/2012 | Csavoy et al. |
| 8,109,877 B2 | 2/2012 | Moctezuma de la Barrera et al. |
| 8,112,292 B2 | 2/2012 | Simon |
| 8,116,430 B1 | 2/2012 | Shapiro et al. |
| 8,120,301 B2 | 2/2012 | Goldberg et al. |
| 8,121,249 B2 | 2/2012 | Wang et al. |
| 8,123,675 B2 | 2/2012 | Funda et al. |
| 8,133,229 B1 | 3/2012 | Bonutti |
| 8,142,420 B2 | 3/2012 | Schena |
| 8,147,494 B2 | 4/2012 | Leitner et al. |
| 8,150,494 B2 | 4/2012 | Simon et al. |
| 8,150,497 B2 | 4/2012 | Gielen et al. |
| 8,150,498 B2 | 4/2012 | Gielen et al. |
| 8,165,658 B2 | 4/2012 | Waynik et al. |
| 8,170,313 B2 | 5/2012 | Kendrick et al. |
| 8,179,073 B2 | 5/2012 | Farritor et al. |
| 8,182,476 B2 | 5/2012 | Julian et al. |
| 8,184,880 B2 | 5/2012 | Zhao et al. |
| 8,202,278 B2 | 6/2012 | Orban, III et al. |
| 8,208,708 B2 | 6/2012 | Homan et al. |
| 8,208,988 B2 | 6/2012 | Jenser |
| 8,219,177 B2 | 7/2012 | Smith et al. |
| 8,219,178 B2 | 7/2012 | Smith et al. |
| 8,220,468 B2 | 7/2012 | Cooper et al. |
| 8,224,024 B2 | 7/2012 | Foxlin et al. |
| 8,224,484 B2 | 7/2012 | Swarup et al. |
| 8,225,798 B2 | 7/2012 | Baldwin et al. |
| 8,228,368 B2 | 7/2012 | Zhao et al. |
| 8,231,610 B2 | 7/2012 | Jo et al. |
| 8,263,933 B2 | 7/2012 | Hartmann et al. |
| 8,239,001 B2 | 8/2012 | Verard et al. |
| 8,241,271 B2 | 8/2012 | Millman et al. |
| 8,248,413 B2 | 8/2012 | Gattani et al. |
| 8,256,319 B2 | 9/2012 | Cooper et al. |
| 8,271,069 B2 | 9/2012 | Jascob et al. |
| 8,271,130 B2 | 9/2012 | Hourtash |
| 8,281,670 B2 | 10/2012 | Arkin et al. |
| 8,282,653 B2 | 10/2012 | Nelson et al. |
| 8,301,226 B2 | 10/2012 | Csavoy et al. |
| 8,311,611 B2 | 11/2012 | Csavoy et al. |
| 8,320,991 B2 | 11/2012 | Jascob et al. |
| 8,332,012 B2 | 12/2012 | Kienzle, III |
| 8,333,755 B2 | 12/2012 | Cooper et al. |
| 8,335,552 B2 | 12/2012 | Stiles |
| 8,335,557 B2 | 12/2012 | Maschke |
| 8,348,931 B2 | 1/2013 | Cooper et al. |
| 8,353,963 B2 | 1/2013 | Glerum |
| 8,358,818 B2 | 1/2013 | Miga et al. |
| 8,359,730 B2 | 1/2013 | Burg et al. |
| 8,374,673 B2 | 2/2013 | Adcox et al. |
| 8,374,723 B2 | 2/2013 | Zhao et al. |
| 8,379,791 B2 | 2/2013 | Forthmann et al. |
| 8,386,019 B2 | 2/2013 | Camus et al. |
| 8,392,022 B2 | 3/2013 | Ortmaier et al. |
| 8,394,099 B2 | 3/2013 | Patwardhan |
| 8,395,342 B2 | 3/2013 | Prisco |
| 8,398,634 B2 | 3/2013 | Manzo et al. |
| 8,400,094 B2 | 3/2013 | Schena |
| 8,414,957 B2 | 4/2013 | Enzerink et al. |
| 8,418,073 B2 | 4/2013 | Mohr et al. |
| 8,450,694 B2 | 5/2013 | Baviera et al. |
| 8,452,447 B2 | 5/2013 | Nixon |
| RE44,305 E | 6/2013 | Foley et al. |
| 8,462,911 B2 | 6/2013 | Vesel et al. |
| 8,465,476 B2 | 6/2013 | Rogers et al. |
| 8,465,771 B2 | 6/2013 | Wan et al. |
| 8,467,851 B2 | 6/2013 | Mire et al. |
| 8,467,852 B2 | 6/2013 | Csavoy et al. |
| 8,469,947 B2 | 6/2013 | Devengenzo et al. |
| RE44,392 E | 7/2013 | Hynes |
| 8,483,434 B2 | 7/2013 | Buehner et al. |
| 8,483,800 B2 | 7/2013 | Jensen et al. |
| 8,486,532 B2 | 7/2013 | Enzerink et al. |
| 8,489,235 B2 | 7/2013 | Voll et al. |
| 8,500,722 B2 | 8/2013 | Cooper |
| 8,500,728 B2 | 8/2013 | Newton et al. |
| 8,504,201 B2 | 8/2013 | Moll et al. |
| 8,506,555 B2 | 8/2013 | Ruiz Morales |
| 8,506,556 B2 | 8/2013 | Schena |
| 8,508,173 B2 | 8/2013 | Goldberg et al. |
| 8,512,318 B2 | 8/2013 | Tovey et al. |
| 8,515,576 B2 | 8/2013 | Lipow et al. |
| 8,518,120 B2 | 8/2013 | Glerum et al. |
| 8,521,331 B2 | 8/2013 | Itkowitz |
| 8,526,688 B2 | 9/2013 | Groszmann et al. |
| 8,526,700 B2 | 9/2013 | Issacs |
| 8,527,094 B2 | 9/2013 | Kumar et al. |
| 8,528,440 B2 | 9/2013 | Morley et al. |
| 8,532,741 B2 | 9/2013 | Heruth et al. |
| 8,541,970 B2 | 9/2013 | Nowlin et al. |
| 8,548,563 B2 | 10/2013 | Simon et al. |
| 8,549,732 B2 | 10/2013 | Burg et al. |
| 8,551,114 B2 | 10/2013 | Ramos de la Pena |
| 8,551,116 B2 | 10/2013 | Julian et al. |
| 8,556,807 B2 | 8/2013 | Scott et al. |
| 8,556,979 B2 | 10/2013 | Glerum et al. |

(56) References Cited

U.S. PATENT DOCUMENTS

| | | |
|---|---|---|
| 8,560,118 B2 | 10/2013 | Green et al. |
| 8,561,473 B2 | 10/2013 | Blumenkranz |
| 8,562,594 B2 | 10/2013 | Cooper et al. |
| 8,571,638 B2 | 10/2013 | Shoham |
| 8,571,710 B2 | 10/2013 | Coste-Maniere et al. |
| 8,573,465 B2 | 11/2013 | Shelton, IV |
| 8,574,303 B2 | 11/2013 | Sharkey et al. |
| 8,585,420 B2 | 11/2013 | Burbank et al. |
| 8,594,841 B2 | 11/2013 | Zhao et al. |
| 8,597,198 B2 | 12/2013 | Sanborn et al. |
| 8,600,478 B2 | 12/2013 | Verard et al. |
| 8,603,077 B2 | 12/2013 | Cooper et al. |
| 8,611,985 B2 | 12/2013 | Lavallee et al. |
| 8,613,230 B2 | 12/2013 | Blumenkranz et al. |
| 8,621,939 B2 | 1/2014 | Blumenkranz et al. |
| 8,624,537 B2 | 1/2014 | Nowlin et al. |
| 8,630,389 B2 | 1/2014 | Kato |
| 8,634,897 B2 | 1/2014 | Simon et al. |
| 8,634,957 B2 | 1/2014 | Toth et al. |
| 8,638,056 B2 | 1/2014 | Goldberg et al. |
| 8,638,057 B2 | 1/2014 | Goldberg et al. |
| 8,639,000 B2 | 1/2014 | Zhao et al. |
| 8,641,726 B2 | 2/2014 | Bonutti |
| 8,644,907 B2 | 2/2014 | Hartmann et al. |
| 8,657,809 B2 | 2/2014 | Schoepp |
| 8,660,635 B2 | 2/2014 | Simon et al. |
| 8,666,544 B2 | 3/2014 | Moll et al. |
| 8,675,939 B2 | 3/2014 | Moctezuma de la Barrera |
| 8,678,647 B2 | 3/2014 | Gregerson et al. |
| 8,679,125 B2 | 3/2014 | Smith et al. |
| 8,679,183 B2 | 3/2014 | Glerum et al. |
| 8,682,413 B2 | 3/2014 | Lloyd |
| 8,684,253 B2 | 4/2014 | Giordano et al. |
| 8,685,098 B2 | 4/2014 | Glerum et al. |
| 8,693,730 B2 | 4/2014 | Umasuthan et al. |
| 8,694,075 B2 | 4/2014 | Groszmann et al. |
| 8,696,458 B2 | 4/2014 | Foxlin et al. |
| 8,700,123 B2 | 4/2014 | Okamura et al. |
| 8,706,086 B2 | 4/2014 | Glerum |
| 8,706,185 B2 | 4/2014 | Foley et al. |
| 8,706,301 B2 | 4/2014 | Zhao et al. |
| 8,717,430 B2 | 5/2014 | Simon et al. |
| 8,727,618 B2 | 5/2014 | Maschke et al. |
| 8,734,432 B2 | 5/2014 | Tuma et al. |
| 8,738,115 B2 | 5/2014 | Amberg et al. |
| 8,738,181 B2 | 5/2014 | Greer et al. |
| 8,740,882 B2 | 6/2014 | Jun et al. |
| 8,746,252 B2 | 6/2014 | McGrogan et al. |
| 8,749,189 B2 | 6/2014 | Nowlin et al. |
| 8,749,190 B2 | 6/2014 | Nowlin et al. |
| 8,761,930 B2 | 6/2014 | Nixon |
| 8,764,448 B2 | 7/2014 | Yang et al. |
| 8,771,170 B2 | 7/2014 | Mesallum et al. |
| 8,781,186 B2 | 7/2014 | Clements et al. |
| 8,781,630 B2 | 7/2014 | Banks et al. |
| 8,784,385 B2 | 7/2014 | Boyden et al. |
| 8,786,241 B2 | 7/2014 | Nowlin et al. |
| 8,787,520 B2 | 7/2014 | Baba |
| 8,792,704 B2 | 7/2014 | Isaacs |
| 8,798,231 B2 | 8/2014 | Notohara et al. |
| 8,800,838 B2 | 8/2014 | Shelton, IV |
| 8,808,164 B2 | 8/2014 | Hoffman et al. |
| 8,812,077 B2 | 8/2014 | Dempsey |
| 8,814,793 B2 | 8/2014 | Brabrand |
| 8,816,628 B2 | 8/2014 | Nowlin et al. |
| 8,818,105 B2 | 8/2014 | Myronenko et al. |
| 8,820,605 B2 | 9/2014 | Shelton, IV |
| 8,821,511 B2 | 9/2014 | von Jako et al. |
| 8,823,308 B2 | 9/2014 | Nowlin et al. |
| 8,827,996 B2 | 9/2014 | Scott et al. |
| 8,828,024 B2 | 9/2014 | Farritor et al. |
| 8,830,224 B2 | 9/2014 | Zhao et al. |
| 8,834,489 B2 | 9/2014 | Cooper et al. |
| 8,834,490 B2 | 9/2014 | Bonutti |
| 8,838,270 B2 | 9/2014 | Druke et al. |
| 8,844,789 B2 | 9/2014 | Shelton, IV et al. |
| 8,855,822 B2 | 10/2014 | Bartol et al. |
| 8,858,598 B2 | 10/2014 | Seifert et al. |
| 8,860,753 B2 | 10/2014 | Bhandarkar et al. |
| 8,864,751 B2 | 10/2014 | Prisco et al. |
| 8,864,798 B2 | 10/2014 | Weiman et al. |
| 8,864,833 B2 | 10/2014 | Glerum et al. |
| 8,867,703 B2 | 10/2014 | Shapiro et al. |
| 8,870,880 B2 | 10/2014 | Himmelberger et al. |
| 8,876,866 B2 | 11/2014 | Zappacosta et al. |
| 8,880,223 B2 | 11/2014 | Raj et al. |
| 8,882,803 B2 | 11/2014 | Iott et al. |
| 8,883,210 B1 | 11/2014 | Truncale et al. |
| 8,888,821 B2 | 11/2014 | Rezach et al. |
| 8,888,853 B2 | 11/2014 | Glerum et al. |
| 8,888,854 B2 | 11/2014 | Glerum et al. |
| 8,894,652 B2 | 11/2014 | Seifert et al. |
| 8,894,688 B2 | 11/2014 | Suh |
| 8,894,691 B2 | 11/2014 | Iott et al. |
| 8,906,069 B2 | 12/2014 | Hansell et al. |
| 8,964,934 B2 | 2/2015 | Ein-Gal |
| 8,992,580 B2 | 3/2015 | Bar et al. |
| 8,996,169 B2 | 3/2015 | Lightcap et al. |
| 9,001,963 B2 | 4/2015 | Sowards-Emmerd et al. |
| 9,002,076 B2 | 4/2015 | Khadem et al. |
| 9,005,113 B2 | 4/2015 | Scott et al. |
| 9,044,190 B2 | 6/2015 | Rubner et al. |
| 9,107,683 B2 | 8/2015 | Hourtash et al. |
| 9,125,556 B2 | 9/2015 | Zehavi et al. |
| 9,131,986 B2 | 9/2015 | Greer et al. |
| 9,215,968 B2 | 12/2015 | Schostek et al. |
| 9,271,633 B2 | 3/2016 | Scott et al. |
| 9,308,050 B2 | 4/2016 | Kostrzewski et al. |
| 9,380,984 B2 | 7/2016 | Li et al. |
| 9,393,039 B2 | 7/2016 | Lechner et al. |
| 9,398,886 B2 | 7/2016 | Gregerson et al. |
| 9,398,890 B2 | 7/2016 | Dong et al. |
| 9,414,859 B2 | 8/2016 | Ballard et al. |
| 9,420,975 B2 | 8/2016 | Gutfleisch et al. |
| 9,492,235 B2 | 11/2016 | Hourtash et al. |
| 9,565,997 B2 | 2/2017 | Scott et al. |
| 9,592,096 B2 | 3/2017 | Maillet et al. |
| 9,750,465 B2 | 9/2017 | Engel et al. |
| 9,757,203 B2 | 9/2017 | Hourtash et al. |
| 9,795,354 B2 | 10/2017 | Menegaz et al. |
| 9,814,535 B2 | 11/2017 | Bar et al. |
| 9,820,783 B2 | 11/2017 | Donner et al. |
| 9,833,265 B2 | 11/2017 | Donner et al. |
| 9,848,922 B2 | 12/2017 | Tohmeh et al. |
| 9,925,011 B2 | 3/2018 | Gombert et al. |
| 9,931,025 B1 | 4/2018 | Graetzel et al. |
| 9,962,069 B2 | 5/2018 | Scott et al. |
| 10,034,717 B2 | 7/2018 | Miller et al. |
| 2001/0036302 A1 | 11/2001 | Miller |
| 2002/0035321 A1 | 3/2002 | Bucholz et al. |
| 2004/0068172 A1 | 4/2004 | Nowinski et al. |
| 2004/0076259 A1 | 4/2004 | Jensen et al. |
| 2005/0096502 A1 | 5/2005 | Khalili |
| 2005/0143651 A1 | 6/2005 | Verard et al. |
| 2005/0154296 A1* | 7/2005 | Lechner ............ A61B 17/00234 600/429 |
| 2005/0171558 A1 | 8/2005 | Abovitz et al. |
| 2006/0100610 A1 | 5/2006 | Wallace et al. |
| 2006/0173329 A1 | 8/2006 | Marquart et al. |
| 2006/0184396 A1 | 8/2006 | Dennis et al. |
| 2006/0241416 A1 | 10/2006 | Marquart et al. |
| 2006/0291612 A1 | 12/2006 | Nishide et al. |
| 2007/0015987 A1 | 1/2007 | Benlloch Baviera et al. |
| 2007/0021738 A1 | 1/2007 | Hasser et al. |
| 2007/0038059 A1 | 2/2007 | Sheffer et al. |
| 2007/0073133 A1 | 3/2007 | Schoenefeld |
| 2007/0156121 A1 | 7/2007 | Millman et al. |
| 2007/0156157 A1 | 7/2007 | Nahum et al. |
| 2007/0167712 A1 | 7/2007 | Keglovich et al. |
| 2007/0233238 A1 | 10/2007 | Huynh et al. |
| 2008/0004523 A1 | 1/2008 | Jensen |
| 2008/0013809 A1 | 1/2008 | Zhu et al. |
| 2008/0033283 A1 | 2/2008 | Dellaca et al. |
| 2008/0046122 A1 | 2/2008 | Manzo et al. |

(56) References Cited

U.S. PATENT DOCUMENTS

| | | |
|---|---|---|
| 2008/0082109 A1 | 4/2008 | Moll et al. |
| 2008/0108912 A1 | 5/2008 | Node-Langlois |
| 2008/0108991 A1 | 5/2008 | von Jako |
| 2008/0109012 A1 | 5/2008 | Falco et al. |
| 2008/0144906 A1 | 6/2008 | Allred et al. |
| 2008/0161680 A1 | 7/2008 | von Jako et al. |
| 2008/0161682 A1 | 7/2008 | Kendrick et al. |
| 2008/0177203 A1 | 7/2008 | von Jako |
| 2008/0214922 A1 | 9/2008 | Hartmann et al. |
| 2008/0228068 A1 | 9/2008 | Viswanathan et al. |
| 2008/0228196 A1 | 9/2008 | Wang et al. |
| 2008/0235052 A1 | 9/2008 | Node-Langlois et al. |
| 2008/0269596 A1 | 10/2008 | Revie et al. |
| 2008/0287771 A1 | 11/2008 | Anderson |
| 2008/0287781 A1 | 11/2008 | Revie et al. |
| 2008/0300477 A1 | 12/2008 | Lloyd et al. |
| 2008/0300478 A1 | 12/2008 | Zuhars et al. |
| 2008/0302950 A1 | 12/2008 | Park et al. |
| 2008/0306490 A1 | 12/2008 | Lakin et al. |
| 2008/0319311 A1 | 12/2008 | Hamadeh |
| 2009/0012509 A1 | 1/2009 | Csavoy et al. |
| 2009/0030428 A1 | 1/2009 | Omori et al. |
| 2009/0080737 A1 | 3/2009 | Battle et al. |
| 2009/0185655 A1 | 7/2009 | Koken et al. |
| 2009/0198121 A1 | 8/2009 | Hoheisel |
| 2009/0216113 A1 | 8/2009 | Meier et al. |
| 2009/0228019 A1 | 9/2009 | Gross et al. |
| 2009/0259123 A1 | 10/2009 | Navab et al. |
| 2009/0259230 A1 | 10/2009 | Khadem et al. |
| 2009/0264899 A1 | 10/2009 | Appenrodt et al. |
| 2009/0281417 A1 | 11/2009 | Hartmann et al. |
| 2009/0306499 A1* | 12/2009 | Van Vorhis ............ A61B 34/20 606/130 |
| 2010/0022874 A1 | 1/2010 | Wang et al. |
| 2010/0039506 A1 | 2/2010 | Sarvestani et al. |
| 2010/0125286 A1 | 5/2010 | Wang et al. |
| 2010/0130986 A1 | 5/2010 | Mailloux et al. |
| 2010/0228117 A1 | 9/2010 | Hartmann |
| 2010/0228265 A1 | 9/2010 | Prisco |
| 2010/0249571 A1 | 9/2010 | Jensen et al. |
| 2010/0274120 A1 | 10/2010 | Heuscher |
| 2010/0280363 A1 | 11/2010 | Skarda et al. |
| 2010/0331858 A1 | 12/2010 | Simaan et al. |
| 2011/0022229 A1 | 1/2011 | Jang et al. |
| 2011/0077504 A1 | 3/2011 | Fischer et al. |
| 2011/0098553 A1 | 4/2011 | Robbins et al. |
| 2011/0137152 A1 | 6/2011 | Li |
| 2011/0213384 A1 | 9/2011 | Jeong |
| 2011/0224684 A1 | 9/2011 | Larkin et al. |
| 2011/0224685 A1 | 9/2011 | Larkin et al. |
| 2011/0224686 A1 | 9/2011 | Larkin et al. |
| 2011/0224687 A1 | 9/2011 | Larkin et al. |
| 2011/0224688 A1 | 9/2011 | Arkin et al. |
| 2011/0224689 A1 | 9/2011 | Arkin et al. |
| 2011/0224825 A1 | 9/2011 | Arkin et al. |
| 2011/0230967 A1 | 9/2011 | O'Halloran et al. |
| 2011/0238080 A1 | 9/2011 | Ranjit et al. |
| 2011/0276058 A1 | 11/2011 | Choi et al. |
| 2011/0282189 A1 | 11/2011 | Graumann |
| 2011/0286573 A1 | 11/2011 | Schretter et al. |
| 2011/0295062 A1 | 12/2011 | Solsona et al. |
| 2011/0295370 A1 | 12/2011 | Suh et al. |
| 2011/0306986 A1 | 12/2011 | Lee et al. |
| 2012/0035507 A1 | 2/2012 | George et al. |
| 2012/0046668 A1 | 2/2012 | Gantes |
| 2012/0051498 A1 | 3/2012 | Koishi |
| 2012/0053597 A1 | 3/2012 | Anvari et al. |
| 2012/0059248 A1 | 3/2012 | Holsing et al. |
| 2012/0071753 A1 | 3/2012 | Hunter et al. |
| 2012/0078236 A1* | 3/2012 | Schoepp ............ A61B 90/50 606/1 |
| 2012/0108954 A1 | 5/2012 | Schulhauser et al. |
| 2012/0136372 A1 | 5/2012 | Amat Girbau et al. |
| 2012/0143084 A1 | 6/2012 | Shoham |
| 2012/0184839 A1 | 7/2012 | Woerlein |
| 2012/0197182 A1 | 8/2012 | Millman et al. |
| 2012/0226145 A1 | 9/2012 | Chang et al. |
| 2012/0235909 A1 | 9/2012 | Birkenbach et al. |
| 2012/0245596 A1 | 9/2012 | Meenink |
| 2012/0253332 A1 | 10/2012 | Moll |
| 2012/0253360 A1 | 10/2012 | White et al. |
| 2012/0256092 A1 | 10/2012 | Zingerman |
| 2012/0294498 A1 | 11/2012 | Popovic |
| 2012/0296203 A1 | 11/2012 | Hartmann et al. |
| 2013/0006267 A1 | 1/2013 | Odermatt et al. |
| 2013/0016889 A1 | 1/2013 | Myronenko et al. |
| 2013/0030571 A1 | 1/2013 | Ruiz Morales et al. |
| 2013/0035583 A1 | 2/2013 | Park et al. |
| 2013/0060146 A1 | 3/2013 | Yang et al. |
| 2013/0060337 A1 | 3/2013 | Petersheim et al. |
| 2013/0094742 A1 | 4/2013 | Feilkas |
| 2013/0096574 A1 | 4/2013 | Kang et al. |
| 2013/0113791 A1 | 5/2013 | Isaacs et al. |
| 2013/0116706 A1 | 5/2013 | Lee et al. |
| 2013/0131695 A1 | 5/2013 | Scarfogliero et al. |
| 2013/0144307 A1 | 6/2013 | Jeong et al. |
| 2013/0158542 A1 | 6/2013 | Manzo et al. |
| 2013/0165937 A1 | 6/2013 | Patwardhan |
| 2013/0178867 A1 | 7/2013 | Farritor et al. |
| 2013/0178868 A1 | 7/2013 | Roh |
| 2013/0178870 A1 | 7/2013 | Schena |
| 2013/0204271 A1 | 8/2013 | Brisson et al. |
| 2013/0211419 A1 | 8/2013 | Jensen |
| 2013/0211420 A1 | 8/2013 | Jensen |
| 2013/0218142 A1 | 8/2013 | Tuma et al. |
| 2013/0223702 A1 | 8/2013 | Holsing et al. |
| 2013/0225942 A1 | 8/2013 | Holsing et al. |
| 2013/0225943 A1 | 8/2013 | Holsing et al. |
| 2013/0231556 A1 | 9/2013 | Holsing et al. |
| 2013/0237995 A1 | 9/2013 | Lee et al. |
| 2013/0245375 A1 | 9/2013 | DiMaio et al. |
| 2013/0261640 A1 | 10/2013 | Kim et al. |
| 2013/0272488 A1 | 10/2013 | Bailey et al. |
| 2013/0272489 A1 | 10/2013 | Dickman et al. |
| 2013/0274761 A1 | 10/2013 | Devengenzo et al. |
| 2013/0281821 A1 | 10/2013 | Liu et al. |
| 2013/0296884 A1 | 11/2013 | Taylor et al. |
| 2013/0303887 A1 | 11/2013 | Holsing et al. |
| 2013/0307955 A1 | 11/2013 | Deitz et al. |
| 2013/0317521 A1 | 11/2013 | Choi et al. |
| 2013/0325033 A1 | 12/2013 | Schena et al. |
| 2013/0325035 A1 | 12/2013 | Hauck et al. |
| 2013/0331686 A1 | 12/2013 | Freysinger et al. |
| 2013/0331858 A1 | 12/2013 | Devengenzo et al. |
| 2013/0331861 A1 | 12/2013 | Yoon |
| 2013/0342578 A1 | 12/2013 | Isaacs |
| 2013/0345717 A1 | 12/2013 | Markvicka et al. |
| 2013/0345757 A1 | 12/2013 | Stad |
| 2014/0001235 A1 | 1/2014 | Shelton, IV |
| 2014/0012131 A1 | 1/2014 | Heruth et al. |
| 2014/0031664 A1 | 1/2014 | Kang et al. |
| 2014/0046128 A1 | 2/2014 | Lee et al. |
| 2014/0046132 A1 | 2/2014 | Hoeg et al. |
| 2014/0046340 A1 | 2/2014 | Wilson et al. |
| 2014/0049629 A1 | 2/2014 | Siewerdsen et al. |
| 2014/0058406 A1 | 2/2014 | Tsekos |
| 2014/0073914 A1 | 3/2014 | Lavallee et al. |
| 2014/0080086 A1 | 3/2014 | Chen |
| 2014/0081128 A1 | 3/2014 | Verard et al. |
| 2014/0088612 A1 | 3/2014 | Bartol et al. |
| 2014/0094694 A1 | 4/2014 | Moctezuma de la Barrera |
| 2014/0094851 A1 | 4/2014 | Gordon |
| 2014/0096369 A1 | 4/2014 | Matsumoto et al. |
| 2014/0100587 A1 | 4/2014 | Farritor et al. |
| 2014/0121676 A1 | 5/2014 | Kostrzewski et al. |
| 2014/0128882 A1 | 5/2014 | Kwak et al. |
| 2014/0135796 A1 | 5/2014 | Simon et al. |
| 2014/0142591 A1 | 5/2014 | Alvarez et al. |
| 2014/0142592 A1 | 5/2014 | Moon et al. |
| 2014/0148692 A1 | 5/2014 | Hartmann et al. |
| 2014/0163581 A1 | 6/2014 | Devengenzo et al. |
| 2014/0171781 A1 | 6/2014 | Stiles |
| 2014/0171900 A1 | 6/2014 | Stiles |
| 2014/0171965 A1 | 6/2014 | Loh et al. |

(56) References Cited

U.S. PATENT DOCUMENTS

| | | |
|---|---|---|
| 2014/0180308 A1 | 6/2014 | von Grunberg |
| 2014/0180309 A1 | 6/2014 | Seeber et al. |
| 2014/0187915 A1 | 7/2014 | Yaroshenko et al. |
| 2014/0188132 A1 | 7/2014 | Kang |
| 2014/0194699 A1 | 7/2014 | Roh et al. |
| 2014/0130810 A1 | 8/2014 | Azizian et al. |
| 2014/0221819 A1 | 8/2014 | Sarment |
| 2014/0222023 A1 | 8/2014 | Kim et al. |
| 2014/0228631 A1 | 8/2014 | Kwak et al. |
| 2014/0234804 A1 | 8/2014 | Huang et al. |
| 2014/0257328 A1 | 9/2014 | Kim et al. |
| 2014/0257329 A1 | 9/2014 | Jang et al. |
| 2014/0257330 A1 | 9/2014 | Choi et al. |
| 2014/0275760 A1 | 9/2014 | Lee et al. |
| 2014/0275985 A1 | 9/2014 | Walker et al. |
| 2014/0276931 A1 | 9/2014 | Parihar et al. |
| 2014/0276940 A1 | 9/2014 | Seo |
| 2014/0276944 A1 | 9/2014 | Farritor et al. |
| 2014/0288413 A1 | 9/2014 | Hwang et al. |
| 2014/0299648 A1 | 10/2014 | Shelton, IV et al. |
| 2014/0303434 A1 | 10/2014 | Farritor et al. |
| 2014/0303643 A1 | 10/2014 | Ha et al. |
| 2014/0305995 A1 | 10/2014 | Shelton, IV et al. |
| 2014/0309659 A1 | 10/2014 | Roh et al. |
| 2014/0316436 A1 | 10/2014 | Bar et al. |
| 2014/0323803 A1 | 10/2014 | Hoffman et al. |
| 2014/0324070 A1 | 10/2014 | Min et al. |
| 2014/0330288 A1 | 11/2014 | Date et al. |
| 2014/0364720 A1 | 12/2014 | Darrow et al. |
| 2014/0371577 A1 | 12/2014 | Maillet et al. |
| 2015/0039034 A1 | 2/2015 | Frankel et al. |
| 2015/0085970 A1 | 3/2015 | Bouhnik et al. |
| 2015/0146847 A1 | 5/2015 | Liu |
| 2015/0150524 A1 | 6/2015 | Yorkston et al. |
| 2015/0196261 A1 | 7/2015 | Funk |
| 2015/0213633 A1 | 7/2015 | Chang et al. |
| 2015/0335480 A1* | 11/2015 | Alvarez et al. |
| 2015/0342647 A1 | 12/2015 | Frankel et al. |
| 2016/0005194 A1 | 1/2016 | Schretter et al. |
| 2016/0166329 A1 | 6/2016 | Langan et al. |
| 2016/0235480 A1 | 8/2016 | Scholl et al. |
| 2016/0249990 A1 | 9/2016 | Glozman et al. |
| 2016/0302871 A1 | 10/2016 | Gregerson et al. |
| 2016/0320322 A1 | 11/2016 | Suzuki |
| 2016/0331335 A1 | 11/2016 | Gregerson et al. |
| 2017/0135770 A1 | 5/2017 | Scholl et al. |
| 2017/0143284 A1 | 5/2017 | Sehnert et al. |
| 2017/0143426 A1 | 5/2017 | Isaacs et al. |
| 2017/0156816 A1 | 6/2017 | Ibrahim |
| 2017/0202629 A1 | 7/2017 | Maillet et al. |
| 2017/0212723 A1 | 7/2017 | Atarot et al. |
| 2017/0215825 A1 | 8/2017 | Johnson et al. |
| 2017/0215826 A1 | 8/2017 | Johnson et al. |
| 2017/0215827 A1 | 8/2017 | Johnson et al. |
| 2017/0231710 A1 | 8/2017 | Scholl et al. |
| 2017/0258426 A1 | 9/2017 | Risher-Kelly et al. |
| 2017/0258535 A1* | 9/2017 | Crawford .............. B25J 15/0441 |
| 2017/0273748 A1 | 9/2017 | Hourtash et al. |
| 2017/0296277 A1 | 10/2017 | Hourtash et al. |
| 2017/0360493 A1 | 12/2017 | Zucher et al. |
| 2018/0228351 A1 | 8/2018 | Scott et al. |
| 2019/0209080 A1* | 7/2019 | Gullotti .............. A61B 17/7035 |

\* cited by examiner

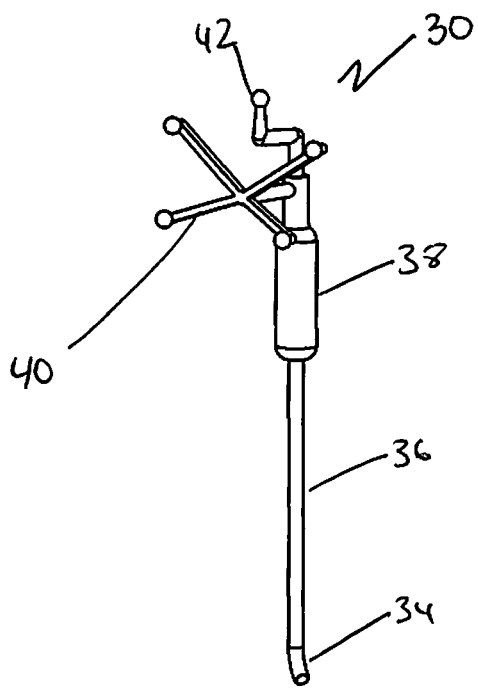
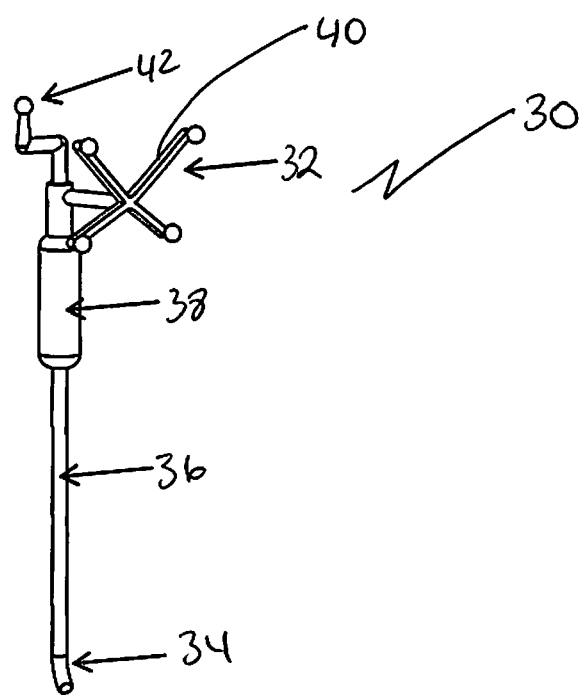
FIG. 2A  FIG. 2B
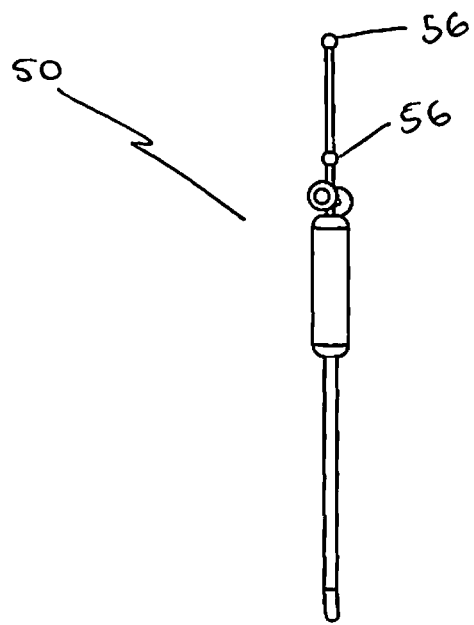
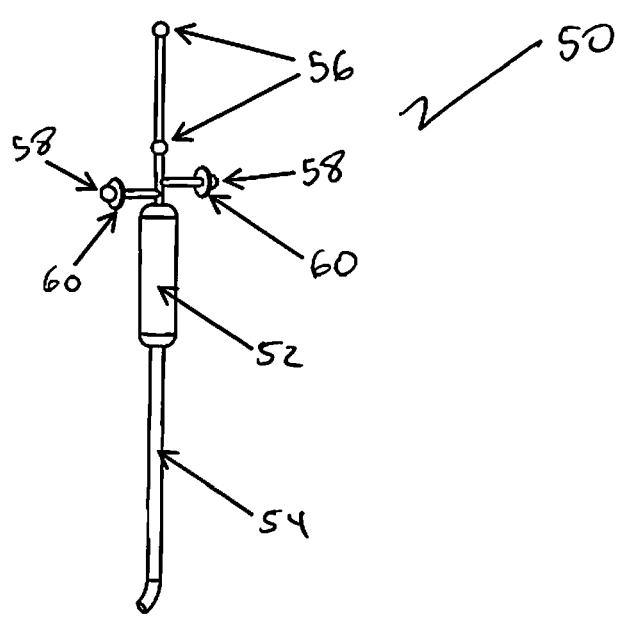
FIG. 3A  FIG. 3B

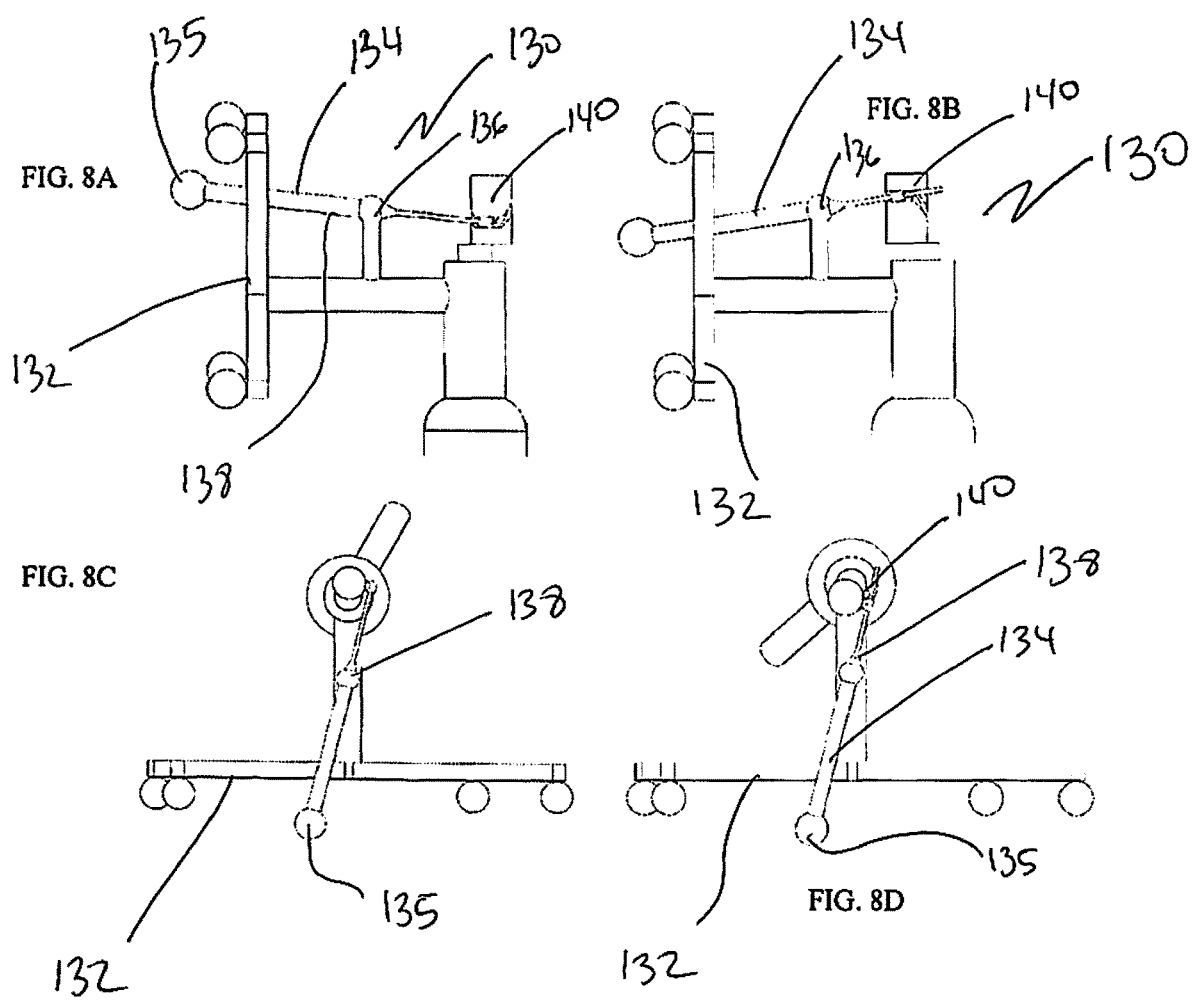

NAVIGATED INSTRUMENT FOR USE IN ROBOTIC GUIDED SURGERY

CROSS REFERENCE TO RELATED APPLICATIONS

This application is a Non-Provisional Application which claims priority to provisional application Ser. No. 62/947,688 filed on a Dec. 13, 2019, which is incorporated in its entirety herein.

FIELD OF THE INVENTION

The present disclosure relates to medical devices, and more particularly to an instrument for use with a robotic surgical system.

BACKGROUND

Position recognition systems for robot assisted surgeries are used to determine the position of and track a particular object in 3-dimensions (3D). In robot assisted surgeries, for example, certain objects, such as surgical instruments, need to be tracked with a high degree of precision as the instrument is being positioned and moved by a robot or by a physician, for example.

Position recognition systems may use passive and/or active sensors or markers for tracking the objects. In passive sensors or markers, objects to be tracked may include passive sensors, such as reflective spherical balls, which are positioned at strategic locations on the object to be tracked. With passive tracking sensors, the system then geometrically resolves the 3-dimensional position of the active and/or passive sensors based on information from or with respect to one or more of the infrared cameras, digital signals, known locations of the active or passive sensors, distance, the time it took to receive the responsive signals, other known variables, or a combination thereof.

These surgical systems can therefore utilize position feedback to precisely guide movement of robotic arms and tools relative to a patients' surgical site. In surgical navigation, commonly tracked tools like a drill, tap or screwdriver are typically axially symmetrical. For example, a representation of a drill looks the same no matter how the drill bit is rotated. The tracking array for such tools may be mobile in its rotational coordinate about the tool since the rotational position of the tool does not need to be monitored. Therefore, marker arrays for tracking these common tools are designed with the array on a sleeve that is free to rotate about the tool. The user may reposition the array about the tool shaft as necessary to keep it facing toward the tracking cameras while using the tool.

However, it is sometimes necessary to track a tool that is not symmetrical, such as a curved curette or a delivery device for an interbody spacer. In such cases, the system must track the full rigid body position of the tool so that it can properly update the image of the tool overlaid on anatomy, showing, for example, which direction the curve or cutting surface of the curette faces. For these tools and instruments, different methods must be used to find the tracking array's orientation relative to the tool in all directions including rotation.

SUMMARY

An instrument for use in a navigated surgical procedure, the instrument includes a proximal portion, a distal portion and a shaft extending therebetween. An angled instrument tip is positioned at an end of the distal portion of the instrument. A first tracking array is coupled to the proximal portion of the instrument and a surveillance array is coupled to the proximal portion of the instrument. The tracking array includes a plurality of tracking markers, and is configured to rotate with respect to a central axis of the instrument.

BRIEF DESCRIPTION OF THE DRAWINGS

The accompanying drawings, which are included to provide a further understanding of the disclosure and are incorporated in a constitute a part of this application, illustrate certain non-limiting embodiments of inventive concepts. In the drawings:

FIGS. 2A and 2B illustrates an embodiment of a surgical instrument with an array having adjustable positions.

FIGS. 3A and 3B illustrates the surgical instrument with centerline markers and offset markers for use with a surgical robotic system according to some embodiments;

FIGS. 8A-8D illustrates yet another embodiment of a surgical instrument according to the present disclosure.

DETAILED DESCRIPTION

Figures 1A, 1B, 1C:
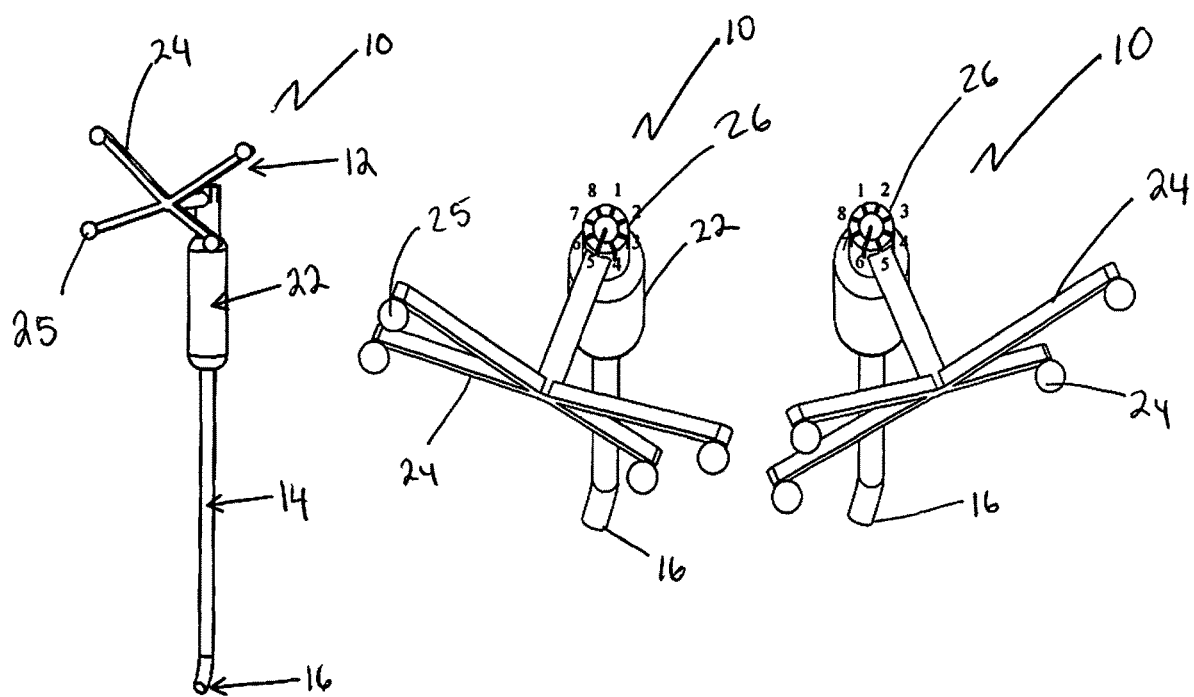
FIGS. 1A, 1B and 1C are views of a surgical instrument according to one embodiment of the present invention.

It is to be understood that the present disclosure is not limited in its application to the details of construction and the arrangement of components set forth in the description herein or illustrated in the drawings. The teachings of the present disclosure may be used and practiced in other embodiments and practiced or carried out in various ways. Also, it is to be understood that the phraseology and terminology used herein is for the purpose of description and should not be regarded as limiting. The use of "including," "comprising," or "having" and variations thereof herein is meant to encompass the items listed thereafter and equivalents thereof as well as additional items. Unless specified or limited otherwise, the terms "mounted," "connected," "supported," and "coupled" and variations thereof are used broadly and encompass both direct and indirect mountings, connections, supports, and couplings. Further, "connected" and "coupled" are not restricted to physical or mechanical connections or couplings.

The following discussion is presented to enable a person skilled in the art to make and use embodiments of the present disclosure. Various modifications to the illustrated embodiments will be readily apparent to those skilled in the art, and the principles herein can be applied to other embodiments and applications without departing from embodiments of the present disclosure. Thus, the embodiments are not intended to be limited to embodiments shown, but are to be accorded the widest scope consistent with the principles and features disclosed herein. The following detailed description is to be read with reference to the figures, in which like elements in different figures have like reference numerals. The figures, which are not necessarily to scale, depict selected embodiments and are not intended to limit the scope of the embodiments. Skilled artisans will recognize the examples provided herein have many useful alternatives and fall within the scope of the embodiments.

In surgical navigation, it is very important that a tool's tracker marker template be accurate so that a tracked tool and/or tracked robot end effector is correctly localized relative to the anatomy. A method is whereby a sequence of simple and rapid test movements using a navigated tool and a tracked rigid guide tube, such as the guide tube of a surgical robot, can fully calibrate a tool that was initially not calibrated. The calibrated tool will have its shaft coincident with one coordinate axis, the markers facing toward a pre-defined direction, and the origin offset by a pre-defined distance from the origin of the tracked rigid guide tube.

Surgical navigation uses an optical tracking system where two or more cameras detect reflective or active markers on tools and track the 3D coordinates of the markers through stereophotogrammetry. As discussed in the previous embodiments, surgical tools are equipped with rigidly mounted arrays of 3 or more reflective or active markers, and the tracking system uses best-fit algorithms to match the detected marker locations to stored templates of ideal marker locations. In this way, the system can determine which tool or tools are in view, and where the tools, as rigid bodies, are located in the coordinate system of the cameras. Virtual landmarks can also be found. For example, from the tracked locations of markers that are mounted on a tool's handle, the system finds the location of the tool shaft and tip in camera space. Once tool locations are known relative to the cameras and registration has been performed to align the coordinate system of the cameras to the coordinate system of the medical image, it is possible to graphically display tool locations overlaid on the medical images.

Several factors can influence the accuracy of surgical navigation. The array of optical markers that is attached to the tool is poorly defined or can become displaced, either in whole or in part, causing errors because the detected markers positions are shifted or do not fit the stored marker template well. Other factors included inconsistent lighting and poor viewing angles of markers. In surgical navigation, errors in tracking of poorly-calibrated navigated tools can be manifested as "wander" of the graphic of the tool when the user rotates the tool within a rigid tube. That is, the display of a tool that is rotated within a rigid tube should not move since the tool is spinning about its axis without translating or bending. If the display does in fact wander, it confirms that the tracked location of the tool's array does not match the stored template for the tool.

Now turning to FIGS. 1A-1C, there is shown a tracking array coupled to an instrument that optimally allows the tracking of the instrument according to one embodiment. When a tracking array is rigidly mounted to a tool, the array is designed so that it is pointing optimally toward the cameras while the tool is held in the most often used position.

FIGS. 1A, 1B, and 1C shows a navigated tool 10 having a proximal portion 12, a middle portion 14, and a distal portion 16. The distal portion 16 of the navigated tool 10 in this embodiment is provided with a curved tip 18. A shaft 20 extends from the curved tip 18 to the proximal portion 12. At the proximal portion of the tool 18, there is a handle 22 and a tracking array 24. The tracking array 24 is configured to be rotated with respect to the longitudinal axis of the navigated tool 10. The adjustable tracking array 24 also includes a calibration dial 26 positioned on an upper surface of the tool 10. The tracking array 24 is also configured to be positioned at any rotational position and may be locked into position and identified by a locking position as marked on the calibration dial 26. When the tracking array 24 is locked in a particular orientation relative to the handle 22, the user may enter or the system detects the rotational coordinate and the system shows a representation of the tool 10 overlaid on the anatomy. As shown in FIG. 1B and FIG. 1C, the tracking array 10 is locked in position 5 (center) or position 6 (right) to allow tracking cameras to maintain a line of sight for tracking the full motion of the tool 10. The tracking array 24 in the present embodiment illustrates a plurality of markers 25. It should be noted that in other embodiments, it is contemplated that the tracker array 24 may having a more than additional or less markers than shown in the current embodiment. The tracker array 24 may also be configured as a different shape than illustrate in FIGS. 1A-1C.

In another embodiment as shown in FIGS. 2A and 2B, a multi-positional array system 30 includes a proximal portion 32, a distal portion 34 and a shaft 36 extending from the proximal portion to the distal portion 34. The distal portion 34 includes a curved tip in one embodiment, but include any type of tip that is suitable for a surgical procedure. The proximal portion also includes a handle 38 and a rotatable tracking array 40, and a fixed marker 42. The fixed marker 42 may be used as an additional tracking marker as a means of automatically identifying the system 30 position relative to the tracking array 40. This additional fixed marker 42 must be offset from the center of rotation of the tracking array (center shaft of the tool) to detect array position.

FIGS. 2A and 2B also shows an embodiment of an array 40 that is rotationally adjustable. The tool array 40 is rotatably movable relative to the handle 38 and shaft 36. A single fixed marker 42 mounted to the central shaft detects the rotational position of the tracking array relative to the shaft, allowing correct tracking and graphical representation of the entire tool including the curved tool tip. Although in the present embodiment the fixed marker 42 is shown in a particular offset location, it is contemplated in other embodiments, that the fixed marker 42 may be configured in type of offset position relative to the tool and tracking array. Also, it the present embodiment, the tracking marker 42 is positioned in a offset position from the upper surface of the tool, it is contemplated in other embodiments that the offset tracking marker 42 may be positioned laterally with respect to the tool 30.

Now turning to FIGS. 3A and 3B, an instrument 50 having a handle 52, a shaft 54 and a plurality of tracking markers is shown. The instrument 50 includes at least two centerline markers 56 and at least two offset markers 58. The offset markers 58 extend a distance away from the central axis of the instrument 50. The offset markers 58 are also provided with shields 60. The centerline markers 56 and offset markers 58 are rigidly attached to the instrument 50. The centerline markers 56 and offset markers 58 are provided with features allowing it to be viewed from a wide range of angles. The offset markers 58 are at different longitudinal coordinates along the centerline, allowing the system to distinguish between the offset markers 58 when only one is visible by the distance from the centerline markers 56.

Alternately, the offset markers 58 could be at different radial distances offset from centerline but at the same longitudinal coordinate to allow them to be distinguished. The thin flat shield 60 behind each offset marker hides the marker from view and prevents visual overlap with other markers or parts of the tool when the tool is rotated away from the cameras. Although in the present embodiment, only two offset markers and centerline makers are shown, it is contemplated that a plurality of either centerline and/or offset makers may be utilized to determine the position of the instrument.

In another embodiment, a part of one offset marker may be visible farther from the cameras due to partial obstruction from its shield and the whole of another offset marker is visible closer to the cameras. The system can utilize the larger detected 2D "blob" (high contrast region) size in deciding which of the two offset markers to use in calculations to get the most accurate navigation. Alternately, the system may also use calculations for both sets of 3 markers (two centerline markers plus offset marker 1 or two centerline markers plus offset marker 2) to determine the tip location of the instrument.

Figure 4:
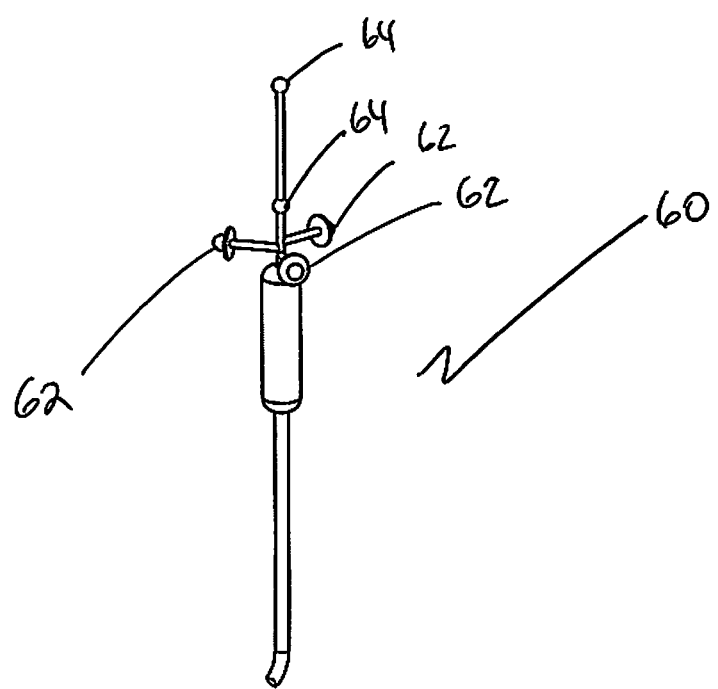
FIG. 4 illustrates another embodiment of the surgical instrument having multiple offset markers and center line markers.

In another embodiment as shown in FIG. 4, there is provided an instrument 60 that utilizes three offset markers 62 at 120° separation, ensuring that at least one of the offset markers is fully visible to both cameras at any orientation. The instrument 60 also includes at least two colinear markers 64 positioned on the central axis of the instrument.

Figure 5A:
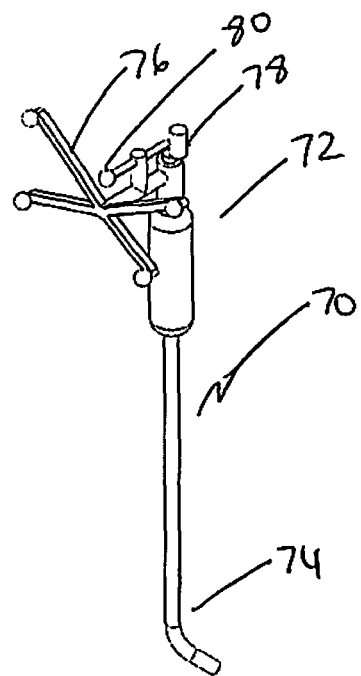
FIGS. 5A, 5B, 5C, and 5D illustrate yet another embodiment of a surgical instrument that allows rotation of an array by use of a cam mechanism.
Figure 5B:
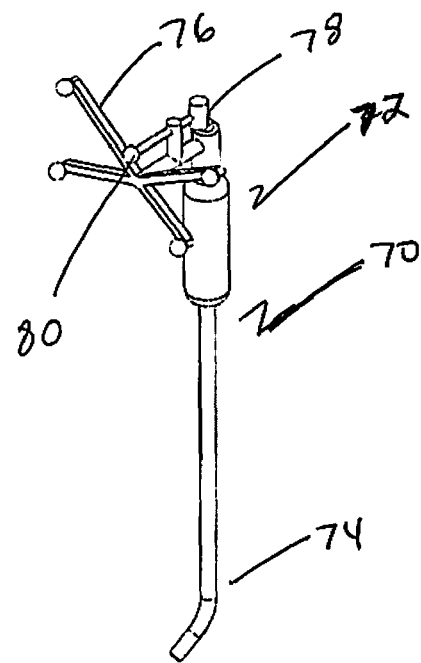
Figure 5C:
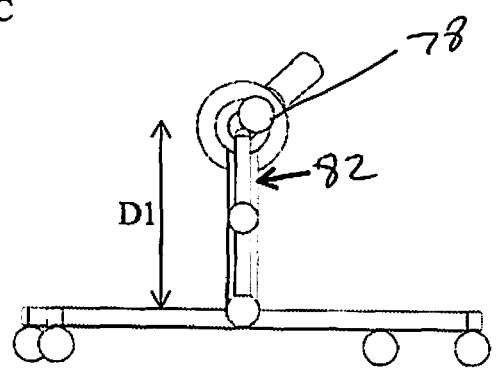
Figure 5D:
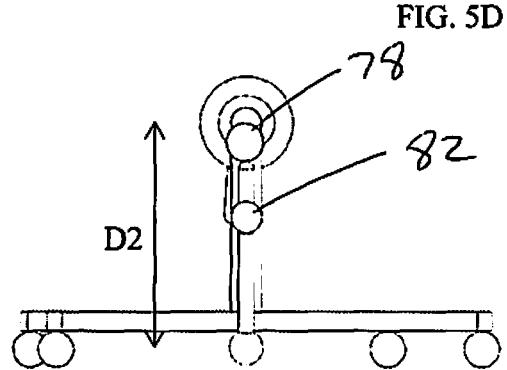
Figure 6A:
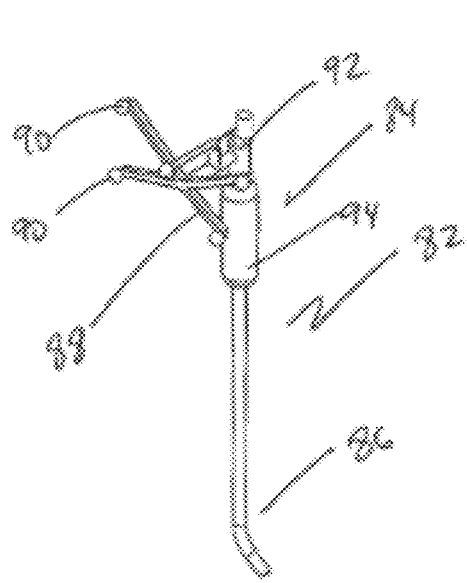
FIGS. 6A, 6B, 6C, and 6D show another embodiment of a surgical instrument that uses a hinged cam mechanism to allow rotation of an array.
Figure 6B:
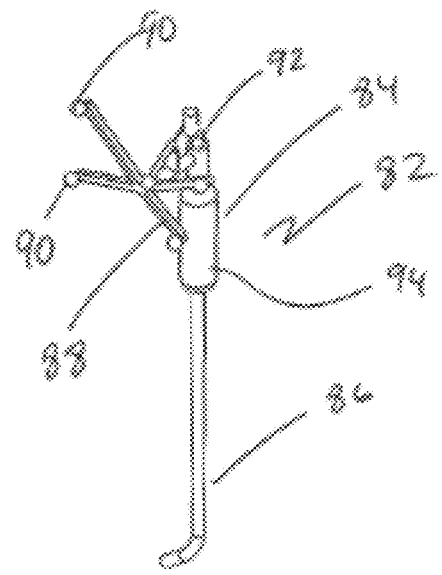
Figure 6C:
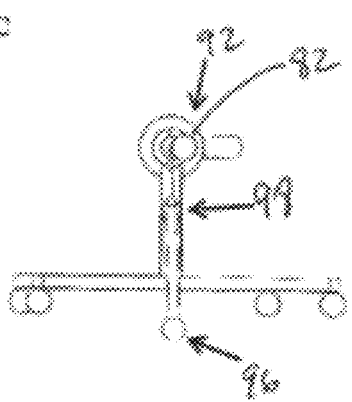
Figure 6D:
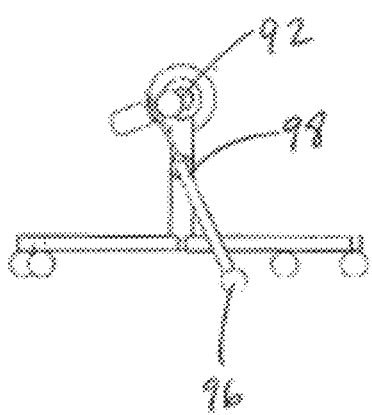

FIGS. 5A and 5B shows an instrument 70 with a proximal portion 72 and a distal portion 74. The proximal portion includes a tracking array 76 and a single cam mechanism 78 that causes an tracked marker 80, which is positioned on a spring-loaded piston 82, to move toward or away from a central shaft of the instrument 70 when the tracking array 76 is rotated about the shaft. The cam mechanism 78 is an offset circular or oblong shaped element on which a spring-loaded plunger 82 presses. This mechanism 78 causes the plunger 82 to move inward and outward by varying amounts as the array orientation is adjusted relative to the instrument tip as shown in FIG. 5C and FIG. 5D. After calibrating the angle of the tracker array relative to marker's 80 linear position, by tracking the offset of the additional marker, the system can determine the orientation of the instrument 70. As the instrument tip is moved and angled as shown as about 135 degrees counterclockwise as shown in FIG. 5C, the marker 80 is offset to position D1. If the instrument tip is angled to about 5 degrees clockwise as shown in FIG. 5D, the marker 80 is moved to offset position D2. As shown in FIGS. 5C and 5D, the cam mechanism 78 is configured to provide information to the tracking system about the orientation of the tip relative to the instrument. In this embodiment, the tracker array 76 is provided with 4 markers, it is contemplated in other embodiments, additional or less markers may be used to navigate the instrument.

FIGS. 6A-6D show an instrument 82 having a proximal portion 84 and a distal portion 86. The proximal portion 84 includes a tracker array 88 that includes a plurality of trackers 90. The proximal portion 84 also includes a single cam mechanism 92 coupled to a handle assembly 94 of the instrument 82. The single cam mechanism 92 is coupled to the upper surface of the handle assembly 94 of the instrument. The cam mechanism 92 is also coupled to a tracking marker 96. Tracking marker 96 is positioned on a hinged, spring-loaded arm 98 and configured to move toward or away from the central shaft of the instrument when the tracker array 88 is rotated about the shaft. As further illustrated in FIGS. 6C and 6D, the spring loaded arm 98 is configured to swivel in varying directions allowing for the tracked marker 96 to be visualized by the camera system at different locations. After calibrating angle of tracker array 88 relative to tracker marker 96 position, by detecting the offset of the marker 96, the system can determine the orientation of the instrument.

With either a linear or hinged mechanism, the moving position of the tracker marker can be detected relative to the positions of the rest of the markers in the tracking array and this information used to determine the orientation of the instrument tip relative to the tracking array. Then, as the surgeon uses the instrument, the tracker array may face toward the cameras while positioning the instrument appropriately to perform surgical work, and the system can continuously track the instrument position while also showing a correct graphical representation of the instrument, including its asymmetrical tip.

Figures 7A, 7B:
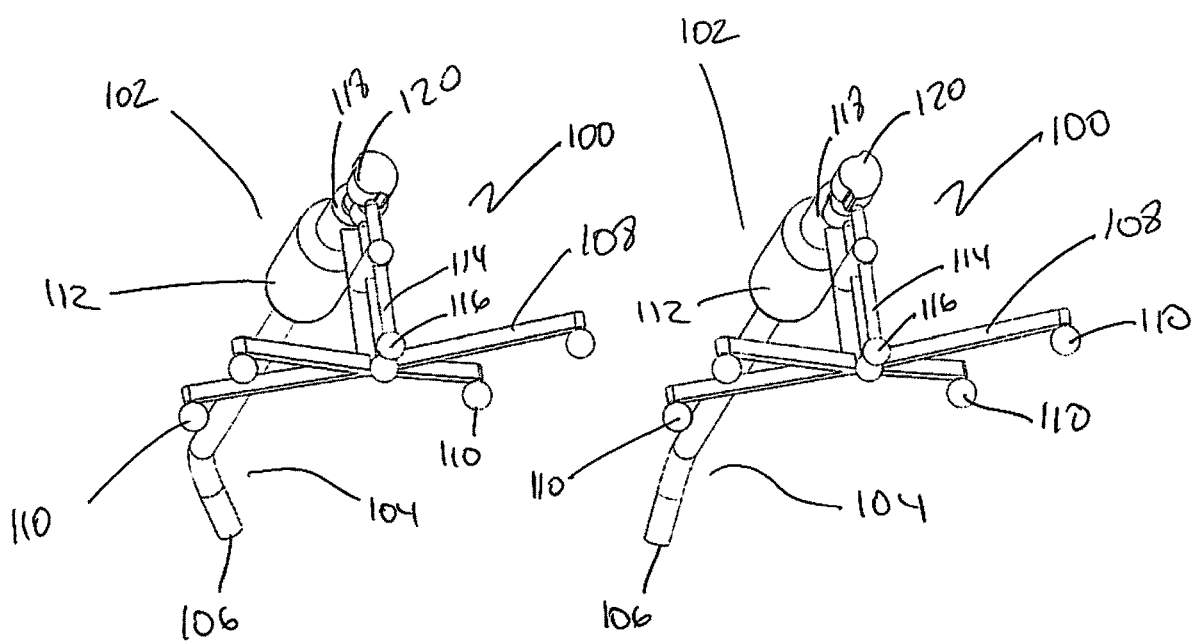
FIGS. 7A and 7B illustrate another embodiment of a surgical instrument that uses multiple cam mechanisms for rotation of an array.

Now turning to FIGS. 7A and 7B, a system for unambiguously defining the instrument tip orientation of an instrument through a full 360 degree range using two cam mechanisms is shown. As show in FIGS. 7A and 7B, a surgical instrument 100 having a proximal portion 102 and a distal portion 104. The distal portion 104 is provided with an angled end or tip 106 for performing surgical procedures. The proximal portion 102 is provided with a first tracking array 108. The first tracking array 108 is provided with a plurality of tracking markers 110. Each of the plurality of tracking makers 110 are spaced apart from one another and configured to be detected by a camera system. The proximal portion 102 of the instrument 100 also includes a handle assembly 112. The proximal portion 102 also includes a second tracker array 114 having at least one tracker marker 116. The second tracker array 114 is coupled to the proximal portion 102 via a first cam mechanism 118 and a second cam mechanism 120. The first cam mechanism 118 is configured to enable the second tracker array 114 to moved vertically with respect to the longitudinal axis of the instrument 100. The second cam mechanism 120 is configured to enable the second tracker array 114 to be moved horizontally with respect to the longitudinal axis of the instrument 100. As each cam mechanism controls the position of tracking marker 116, the positions of the marker 116 can be identified relative to the tracking array 108.

In another embodiment, the second cam mechanism may be configured to shift the whole assembly of the first cam mechanism, thereby, the first cam mechanism may shift the marker 116 inward and outward along a piston toward or away from the tracker array 108, whereas the second cam mechanism could shift the marker 116 longitudinally up or down in the direction of the instrument relative to the tracker array 108.

Now turning to FIGS. 8A-8D, another embodiment for determining the rotational positioning of an instrument 130 is provided. FIGS. 8A-8D illustrates a proximal portion of the instrument 130. The instrument 130 includes a first tracker array 132 and a second tracker array 134 with a tracker marker 135. Tracker marker 135 is attached to a hinged cam assembly 136. The hinged cam assembly 136 includes a lever arm 138 attached to the cam mechanism 140. As the instrument is rotated, the tracker marker 135 is moved rotationally and angularly with respect to the central longitudinal axis of the instrument 130. As a result, the tracker marker 135 along with the first tracker array 132, is tracked by the camera system allowing the instrument tip to accurately tracked during surgical procedures.

Figure 9:
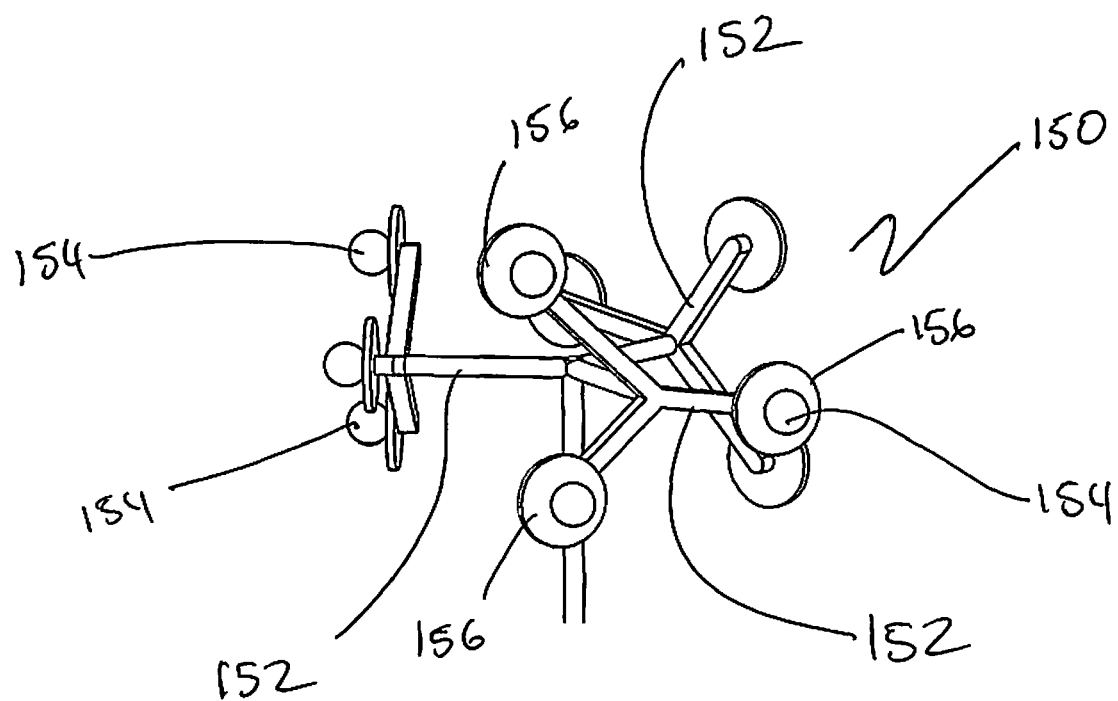
FIG. 9 illustrates another embodiment of a surgical instrument with a plurality of tracker arrays.

In yet another embodiment, FIG. 9 illustrates an instrument 150 having multiple tracking arrays 152. Each of the tracking arrays 152 is configured with a plurality of tracking markers 154, with each tracking marker 154 having a shield 156. The tracking arrays 152 are deployed about the center axis of the instrument 150. In one embodiment, the system would select for tracking only the 3 or more markers closest to the cameras and in best view of the cameras. The tracking arrays 152 in this embodiment provide 3 markers each however it is contemplated in other embodiments to have additional or less markers for each tracking array 152. The tracking arrays 152 are also configured to be detected by a camera system from all angles.

Figure 10:
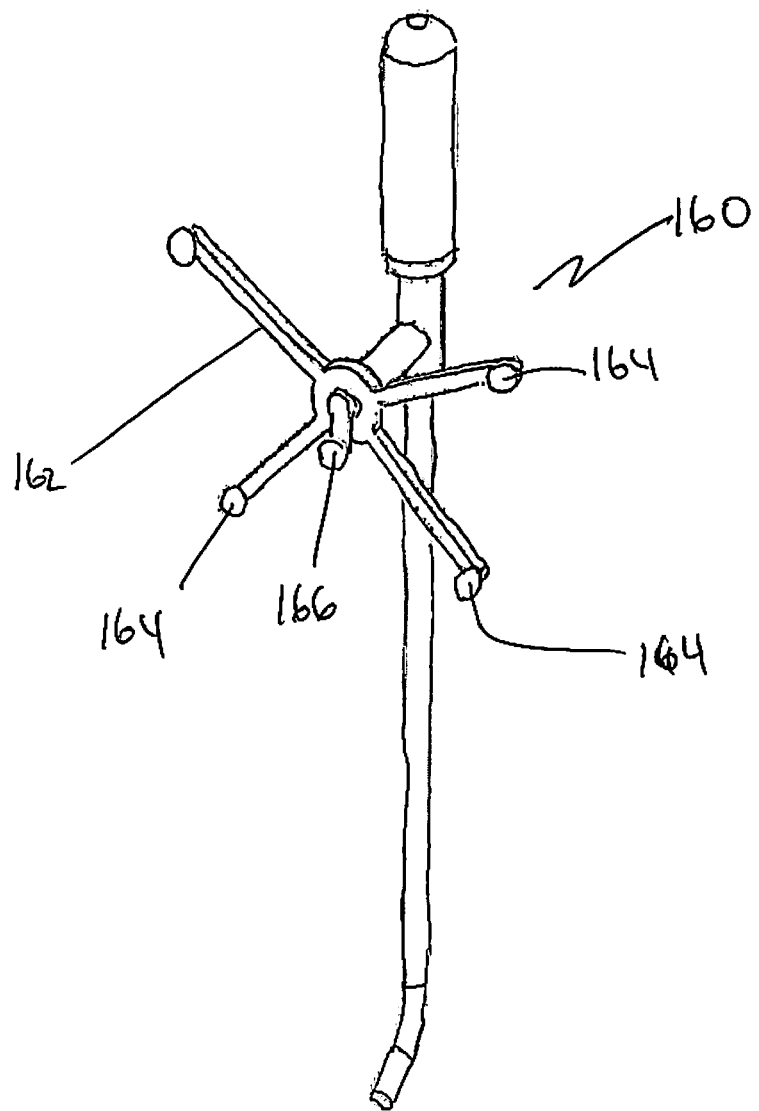
FIG. 10 illustrates yet another embodiment of a surgical instrument in which the array is configured to swivel about central axis of the surgical instrument.

FIG. 10 shows an embodiment in which surgical instrument 160 includes a tracker array 162 that is capable of rotating with respect to the longitudinal axis of the instrument. The tracker array 162 includes plurality of markers 164 and a surveillance marker 166 positioned on a central portion of the tracker array 162. The surveillance marker 166 is configured to rotated with respect to the tracker array 162 and is configured to identify the array position relative to the instrument tip. The surveillance marker 166 is mounted directly to the tracker array 162 face on the central portion of the tracker array 162. In other embodiments, it is contemplated that the surveillance marker 166 is configured to rotated and translated with respect to the instrument 160.

Now turning to FIG. 11, a tracking system and method of performing a procedure to optimize the tracking of markers is provided. When an optical tracking system tracks the markers on a tool or instrument, it performs a comparison of the detected markers to the known stored marker template for that tool or instrument using computational methods. Other important landmarks of the tool or instrument such as its tip and tail are designed to be in known locations in the template coordinate system. During any tracking frame, using computational methods, the system transforms the coordinates of any landmark defined within the template coordinate system to camera space based on the tool's detected markers in that frame.

In one embodiment of the invention, the positioning of physical features of the tool within the coordinate system of the marker template can serve to re-define the tool template during a simple calibration procedure. These features of the tool are defined such that it is exactly aligned with and positioned along the Cartesian coordinate (X,Y,Z) axes according to standards used for registration. The navigated tool or instrument includes a shaft that is aligned along the Z axis, with a tail that is configured to be in a more positive position than the tip of the tool or instrument. The marker array coupled to the instrument is aligned at a rotational position about the Z axis at which the marker's plane normal is aligned in a X direction. The tool or instrument is positioned longitudinally along the Z axis with its Z origin (Z=0) at the location where the tool bottoms out on the guide tube.

Using a tool or instrument as provided, the following sequences may be applied in one embodiment of the invention. The system may record the end effector markers or calibration tool markers to establish where an inserted tool bottoms out relative to the end effector guide tube 170. Next, the navigated tool is inserted until it bottoms out in the tube. Then the tool or instrument may be swiveled back and forth about its shaft between 45-90° while keeping the tool or instrument bottomed out.

The data is recorded from these steps in tracking the instrument and used to create an updated tool or instrument template file using the following algorithm. The helical axis of motion in the camera space from the frames of data recoding the swiveling of the instrument is recoded. The axis represents the functional center of the tool or instrument shaft. Next, the system transforms the helical axis into alignment with the Z-axis and these transformations are applied to each data set. Then the instrument or tool is translated along the Z-axis unit it bottoms out and matches the bottom out point of the end effector. Next, the tool is rotated to position the marker array in the positive X direction. After these transformations are applied to the point set, the marker positions in the tool template file are replaced with the marker position in the new coordinate system.

It is also contemplated that software may "repair" the calibration of a tool if it is discovered during usage that the calibration is off. In one embodiment, the user would indicate to software that a repair is being initiated, possibly by pressing a button or otherwise activating a feature that sets a flag indicating that the repair should occur on the next tool coming into close proximity with the end effector guide tube. When a tool is bottomed out in the guide tube, the origin of the tool and the origin of the guide tube should be nearly coincident if the guide tube's origin is also defined as the tube's center and upper rim, or the point where any tool entering it bottoms out.

In the first step of a repair workflow, it is noted that it should be specified which markers belong to the tool's array. Providing the current (damaged) template for the purpose of sorting and matching incoming markers is one possible way to specify the desired markers since each frame can be compared to the damaged template and only markers that are within a tolerance of matching the template pattern can be automatically selected. Alternately, a software interface could take a static shot and markers belonging to the tool could be manually marked on a software interface; software monitors and tracks the markers as they move. In another embodiment, the system may utilize elements that strobe in a known pattern, allowing markers to be indexed and always stored in the same order for each frame. In such systems, the list indices of markers belonging to the tool could be specified.

In later steps, the helical axis of motion (HAM) is calculated. Computational methods used for calculating the finite HAM or approximating the instantaneous HAM from tracked marker data are applied, and better accuracy is achieved with larger angular step sizes.

In some embodiments, instead of repairing an existing template, the swivel method can be used to successfully create an accurate tool marker template without any starting template. Therefore, such a method could construct an accurate marker template for a tool with markers arbitrarily glued, bolted or otherwise secured to its tool shaft as long as the tool bottoms out at a known position and has a central shaft that can be swiveled. If the length of a tool from the location where it bottoms out (its origin) to the tip and the tool's shaft diameter is provided, then all of the critical information about the tool for safe navigation is specified. A generic tool appearing overlaid on the anatomy as a cylinder of specified diameter with the tip offset at the specified distance from the origin could be overlaid on the anatomy to represent the tool and accurately visualize the anatomy intersected by the tool.

Incorporating various methods of tracking the array as well as asymmetric tip orientation and allowing the updating of the CAD model in the software is more accurate in two main orientations, and depending on array pattern in respect to the camera, allows the surgeon to track in a wider variety of positions. Tracking such as this is especially helpful during tracking where the CAD model orientation updates automatically without UI input from the surgeon.

In the above-description of various embodiments of present inventive concepts, it is to be understood that the terminology used herein is for the purpose of describing particular embodiments only and is not intended to be limiting of present inventive concepts. Unless otherwise defined, all terms (including technical and scientific terms) used herein have the same meaning as commonly understood by one of ordinary skill in the art to which present inventive concepts belong. It will be further understood that terms, such as those defined in commonly used dictionaries, should be interpreted as having a meaning that is consistent with their meaning in the context of this specification and the relevant art and will not be interpreted in an idealized or overly formal sense unless expressly so defined herein.

When an element is referred to as being "connected", "coupled", "responsive", or variants thereof to another element, it can be directly connected, coupled, or responsive to the other element or intervening elements may be present. In contrast, when an element is referred to as being "directly connected", "directly coupled", "directly responsive", or variants thereof to another element, there are no intervening elements present. Like numbers refer to like elements throughout. Furthermore, "coupled", "connected", "responsive", or variants thereof as used herein may include wirelessly coupled, connected, or responsive. As used herein, the singular forms "a", "an" and "the" are intended to include the plural forms as well, unless the context clearly indicates otherwise. Well-known functions or constructions may not be described in detail for brevity and/or clarity. The term "and/or" includes any and all combinations of one or more of the associated listed items.

It will be understood that although the terms first, second, third, etc. may be used herein to describe various elements/operations, these elements/operations should not be limited by these terms. These terms are only used to distinguish one element/operation from another element/operation. Thus a first element/operation in some embodiments could be termed a second element/operation in other embodiments without departing from the teachings of present inventive concepts. The same reference numerals or the same reference designators denote the same or similar elements throughout the specification.

As used herein, the terms "comprise", "comprising", "comprises", "include", "including", "includes", "have", "has", "having", or variants thereof are open-ended, and include one or more stated features, integers, elements, steps, components or functions but does not preclude the presence or addition of one or more other features, integers, elements, steps, components, functions or groups thereof. Furthermore, as used herein, the common abbreviation "e.g.", which derives from the Latin phrase "exempli gratia," may be used to introduce or specify a general example or examples of a previously mentioned item, and is not intended to be limiting of such item.

Although several embodiments of inventive concepts have been disclosed in the foregoing specification, it is understood that many modifications and other embodiments of inventive concepts will come to mind to which inventive concepts pertain, having the benefit of teachings presented in the foregoing description and associated drawings. It is thus understood that inventive concepts are not limited to the specific embodiments disclosed hereinabove, and that many modifications and other embodiments are intended to be included within the scope of the appended claims. It is further envisioned that features from one embodiment may be combined or used with the features from a different embodiment(s) described herein. Moreover, although specific terms are employed herein, as well as in the claims which follow, they are used only in a generic and descriptive sense, and not for the purposes of limiting the described inventive concepts, nor the claims which follow. The entire disclosure of each patent and patent publication cited herein is incorporated by reference herein in its entirety, as if each such patent or publication were individually incorporated by reference herein. Various features and/or potential advantages of inventive concepts are set forth in the following claims.

We claim:

1. An instrument for use in a navigated surgical procedure, the instrument comprising:
   a proximal portion, a distal portion and a shaft extending therebetween;
   a first tracking array coupled to the proximal portion of the instrument;
   an instrument tip at an end of the distal portion of the instrument; and
   a cam mechanism coupled to the proximal portion of the instrument;
   wherein the first tracking array includes a plurality of first tracking markers and is configured to rotate with respect to a central axis of the instrument, and
   wherein the cam mechanism has a second tracking marker positioned on a spring loaded arm and is configured to move toward or away from the central axis of the instrument when the first tracking array is rotated about the shaft around the central axis of the instrument.

2. The instrument of claim 1, wherein the plurality of first tracking markers are optical markers.

3. The instrument of claim 1, wherein the first tracking array is configured to be rotated 360 degrees with respect to the central axis of the instrument.

4. The instrument of claim 1, wherein the spring loaded arm is hinged.

5. The instrument of claim 1, wherein the cam mechanism is positioned on a handle of the instrument.

6. The instrument of claim 1, wherein the spring loaded arm is configured to swivel in varying directions allowing for the second tracking marker to be visualized by a camera system at different locations.

7. The instrument of claim 1, wherein the first tracking array and the second tracking marker are configured to be recognized by a camera system associated with a surgical robot.

8. The instrument of claim 1, wherein a surgical robotic navigation system is configured to determine an orientation of the instrument based on an offset of second tracking marker from the first tracking array.

9. An instrument for use in a navigated surgical procedure, the instrument comprising:
   a proximal portion, a distal portion and a shaft extending therebetween;
   a first tracking array coupled to the proximal portion of the instrument;
   an instrument tip at an end of the distal portion of the instrument; and
   a rotatable and translatable cam coupled to the proximal portion of the instrument;
   wherein the first tracking array includes a plurality of first tracking markers and is configured to rotate with respect to a central axis of the instrument,
   wherein the cam has a second tracking marker positioned on an arm and is configured to move toward or away from the central axis of the instrument when the first tracking array is rotated about the shaft around the central axis of the instrument.

10. The instrument of claim 9, wherein the plurality of first tracking markers are optical markers.

11. The instrument of claim 9, wherein the first tracking array is configured to be rotated 360 degrees with respect to the central axis of the instrument.

12. The instrument of claim 9, wherein the spring loaded arm is hinged.

13. The instrument of claim 9, wherein the cam is positioned on a handle of the instrument.

14. The instrument of claim 9, wherein the spring loaded arm is configured to swivel in varying directions allowing for the second tracking marker to be visualized by a camera system at different locations.

15. The instrument of claim 9, wherein the first tracking array and the second tracking marker are configured to be recognized by a camera system associated with a surgical robot.

16. The instrument of claim 9, wherein a surgical robotic navigation system is configured to determine an orientation of the instrument based on an offset of second tracking marker from the first tracking array.

17. The instrument of claim 1, wherein the spring loaded arm rotates about an axis of rotation that is parallel to the central axis of the instrument.

* * * * *